US008658106B2

(12) United States Patent  (10) Patent No.: US 8,658,106 B2
Van Zijl  (45) Date of Patent: Feb. 25, 2014

(54) SYSTEM AND METHOD FOR SANITIZING A HANDLE

(75) Inventor: Eric H. Van Zijl, Ontario (CA)

(73) Assignee: Van Z Solutions, Barrie (CA)

( * ) Notice: Subject to any disclaimer, the term of this patent is extended or adjusted under 35 U.S.C. 154(b) by 461 days.

(21) Appl. No.: 12/973,472

(22) Filed: Dec. 20, 2010

(65) Prior Publication Data

US 2011/0150698 A1  Jun. 23, 2011

Related U.S. Application Data

(60) Provisional application No. 61/288,599, filed on Dec. 21, 2009.

(51) Int. Cl.
*A61L 2/00* (2006.01)
(52) U.S. Cl.
USPC ............ 422/292; 422/107; 422/114; 422/300
(58) Field of Classification Search
USPC ................... 422/28, 107, 114, 115, 292, 300; 379/439
See application file for complete search history.

(56) References Cited

U.S. PATENT DOCUMENTS

| 5,314,668 | A | 5/1994 | Biermaier |
| 5,808,553 | A | 9/1998 | Cunningham |
| 6,874,697 | B2 | 4/2005 | Callueng |
| 7,289,628 | B2 | 10/2007 | Lin et al. |
| 7,320,418 | B2 | 1/2008 | Sassoon |
| 7,360,674 | B2 | 4/2008 | Sassoon |
| 2006/0153733 | A1 | 7/2006 | Sassoon |
| 2006/0267299 | A1 | 11/2006 | Dunser |
| 2008/0023497 | A1 | 1/2008 | Sassoon |
| 2008/0023505 | A1 | 1/2008 | Sasoon |
| 2008/0136649 | A1 | 6/2008 | Van De Hey |
| 2009/0265990 | A1 | 10/2009 | Stratmann |
| 2010/0008822 | A1* | 1/2010 | Hyde et al. ............. 422/292 |

* cited by examiner

*Primary Examiner* — Walter D Griffin
*Assistant Examiner* — Timothy Cleveland
(74) *Attorney, Agent, or Firm* — Wilfred P. So; Blake, Cassels & Graydon LLP

(57) ABSTRACT

A system and method are provided for sanitizing a gas pump handle. A cover at least partially encloses the gas pump handle. The cover is able to be moved from a covered position to an uncovered position. Located on the cover are one or more nozzles or foggers for dispensing sanitizing fluid onto the handle. Sensors detect the position of the cover or the detect whether or not the handle is in the rest position. A controller, in communication with the sensors, sends a command to a pump to spray sanitizer through the nozzle or foggers after a user has pumped gas and returned the handle or the cover to the rest position.

19 Claims, 20 Drawing Sheets

SYSTEM AND METHOD FOR SANITIZING A HANDLE

CROSS-REFERENCE TO RELATED APPLICATIONS

This application claims priority from U.S. Provisional Application No. 61/288,599 filed on Dec. 21, 2009, which is incorporated herein by reference in its entirety.

TECHNICAL FIELD

The following relates to systems and methods for sanitizing hands or handles, or both.

BACKGROUND

Surfaces that are handled or touched by various people may become covered by germs, bacteria and viruses. The germs, bacteria, or viruses, or combinations thereof are collectively hereon referred to as contaminants. For example, a person whose hands are covered with contaminants will touch a surface and transfer the contaminants onto the surface. When another person touches the same surface, at least some of the contaminants on the surface can transfer onto the other person's hands. The contaminants may cause the other person to become sick or ill.

Ensuring that such surfaces are cleaned or sanitized will reduce the spread of contaminants. The spread of the contaminants can also be reduced by cleaning or sanitizing a person's hand or hands. Such approaches may reduce the risk of a person becoming sick. However, cleaning or sanitizing surfaces and hands may be difficult and inconvenient. For example, surfaces that are frequently used (e.g. touched) by people would leave little time for someone to manually clean such surfaces between uses. Moreover, people would find it inconvenient to regularly clean their hands before or after touching a surface. For example, a person may forget to clean their hands on such a frequent basis, or there may not be any cleaning stations or cleaning fluids available when desired.

BRIEF DESCRIPTION OF THE DRAWINGS

Embodiments will now be described by way of example only with reference to the appended drawings wherein.

DETAILED DESCRIPTION OF THE DRAWINGS

Figure 1:
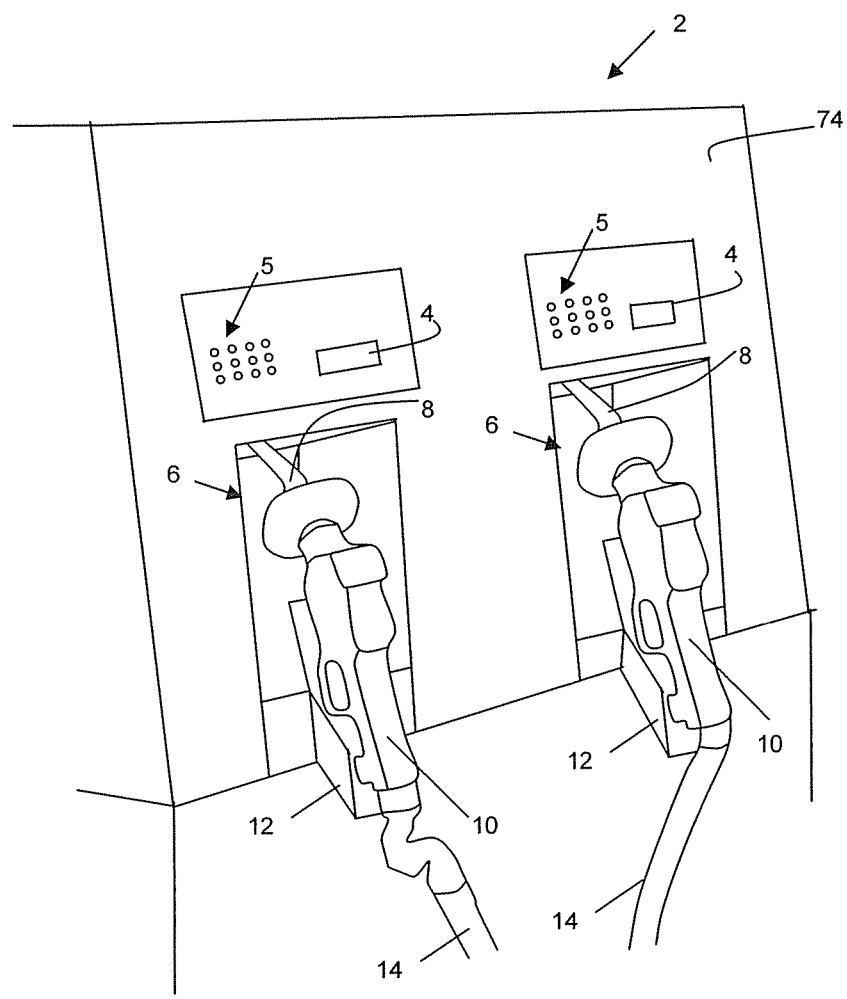
FIG. 1 is a perspective view of a gas pump station.

It will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

In FIG. 1, an example of a gas pump terminal 2 is shown with two gas pump handles 10. The handles 10 are shown here in an unused or resting position at the terminal 2. It can be appreciated that a gas pump terminal 2 would have at least one gas pump handle 10 and that some terminals 2 may have multiple handles 10. Each gas pump handle 10 typically has attached a nozzle 8 from which gas or fuel flows out. A gas hose 14 is also attached to the handle 10. Gas, diesel, or fuel, herein referred to as gas, flows from a gas reservoir through a gas hose 14, and then through the handle 10 before flowing out through the nozzle 8. When not in use, the gas handle 10 sits on a support 12. The support 12 may extend from a front face 74 of the terminal 2. In some gas pump terminals 2, the nozzle 8 is at least partially nested or positioned within a cavity or hollow 6 that is defined in the front face 74. In the embodiment shown in FIG. 1, the hollow 6 is rectangular-like in geometry.

Also shown in FIG. 1 is a display panel 4 and user interface 5 located on the front face 74 of the terminal 2. The display panel 4 may show various information, including for example the type of gas selected for pumping and the cost of the gas. The user interface 5 may comprise selection buttons, a partial or full keyboard, a touch screen, or a microphone and a speaker for voice activated commands. A user can interact with the interface 5 to select a certain type of gas for pumping as well make payments for the gas.

Typically, a user pumps gas by picking up the handle 10, either before or after selecting a type of gas, from the support 12. In some gas terminals 2, a sensor (not shown) detects the presence or removal of the handle 10 from the front face 74. Such a sensor may be a pressure sensor, a mechanical switch sensor, an infrared sensor, a magnetic field sensor, a light beam sensor, etc. It can be appreciated that any sensor that can detect the removal or presence of the handle 10 in the gas terminal 2 is applicable to the principles described herein. When the handle 10 is removed, the gas is allowed to flow. Then the user presses a lever or a switch on the gas handle 10 to allow gas to flow out from the nozzle 8. When the user is finished pumping gas, the handle 10 is returned to its unused or resting position.

Afterwards, another user can pick up the handle 10 to pump the gas in a similar way. It can be appreciated that contaminants (e.g. germs, bacteria and viruses) may be transferred from one user to the handle 10, and then from the handle 10 to another user. Manually sanitizing the handle 10 in between each use is inconvenient and difficult because of the frequent usage of the gas pump.

To address or mitigate at least some of these drawbacks, a system for sanitizing a pump handle is provided. The system comprises one or more nozzles positioned on a pump terminal and oriented to dispense sanitizer on the handle when the handle is resting at the terminal. There is also at least one pump fluidly connected to the one or more nozzles to pump sanitizer from a reservoir to one or more nozzles, as well as a controller for activating the at least one pump.

In another embodiment, a system is provided for sanitizing a pump handle comprising a cover attachable to a pump terminal, whereby the cover is able to move between a covered position and an uncovered position when attached to the pump terminal. The covered position at least partially encloses the handle and the uncovered position allows the handle to be accessed. There are also one or more nozzles positioned on the cover and oriented to dispense sanitizer on the handle when the handle is resting at the terminal. The system also includes at least one pump fluidly connected to the one or more nozzles to pump sanitizer from a reservoir to the one or more nozzles, as well as a controller for activating the at least one pump.

A kit of parts for sanitizing a pump handle is also provided comprising one or more nozzles able to be positioned on a pump terminal or on a cover attachable to the pump terminal. The one or more nozzles are able to be oriented to dispense sanitizer on the handle when the handle is resting at the terminal. The kit of parts also includes at least one pump able to be fluidly connected to the one or more nozzles to pump sanitizer. A reservoir is also provided that is able to be fluidly connected to the at least one pump, wherein the reservoir is able to hold sanitizer. The kit of parts also includes a controller that is able to be connected in data communication with the at least one pump, and is able to activate the at least one pump.

A method for sanitizing a pump handle is provided comprising a controller detecting through a sensor if the handle is positioned at a pump terminal. If not, the controller detects the return of the handle at the terminal, and then activates at least one pump to spray sanitizer through one or more nozzles at the handle.

Another method for sanitizing a pump handle is provided comprising a controller detecting through a sensor if a cover is in a covered position or in an uncovered position, wherein the covered position at least partially encloses the handle and the uncovered position allows the handle to be accessed. If the cover is in the uncovered position, the controller detects the return of the cover to the covered position before activating at least one pump to spray sanitizer through one or more nozzles at the handle.

In another embodiment, a method for sanitizing a pump handle is provided comprising a controller detecting if a user has selected a gas type through a user interface at a gas pump terminal. If so, the controller activates at least one pump to spray sanitizer through one or more nozzles at the handle.

Figure 2:
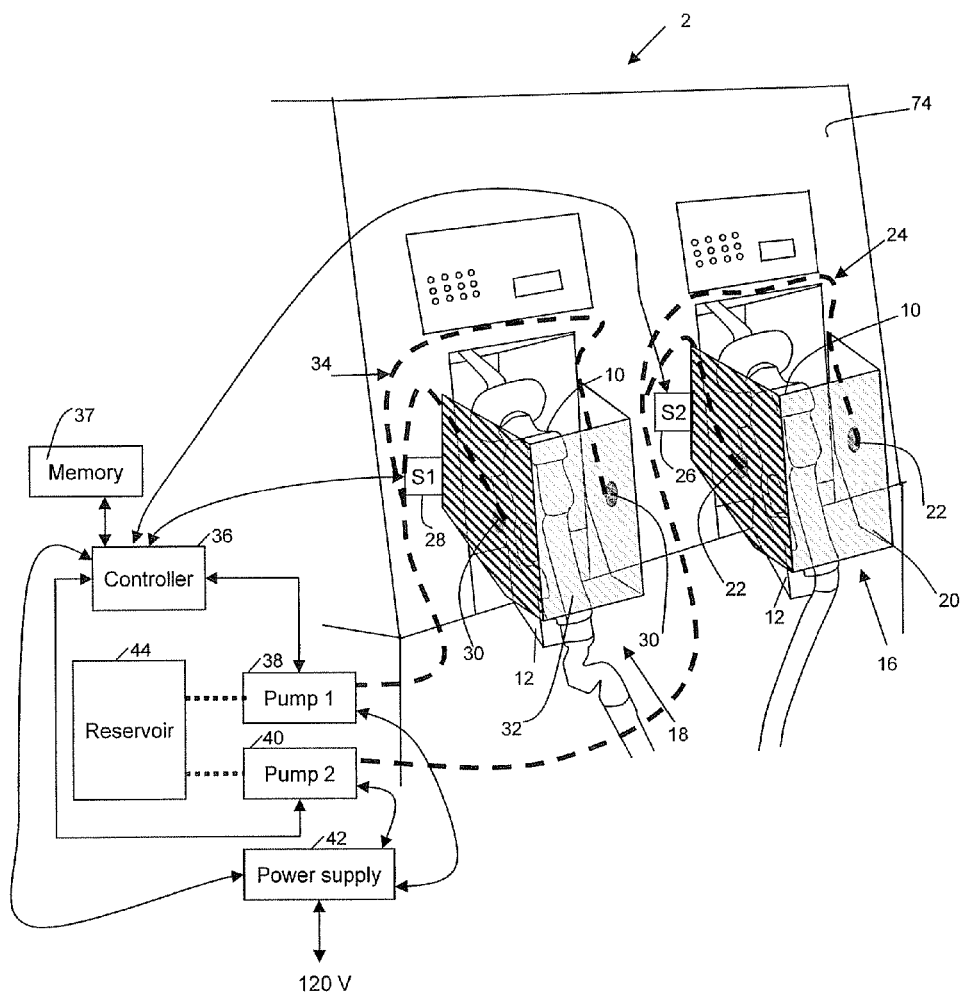
FIG. 2 is a schematic diagram of a gas pump station and an embodiment of a system for sanitizing one or more gas pump handles.

FIG. 2 depicts an example of a sanitizing system for a gas pump handle 10. On the front face 74 of the terminal 2, there is attached a first handle cover assembly 18 for a gas handle 10, and a second handle cover assembly 16 for another gas handle 10. It can be appreciated that there may be multiple cover assemblies, and that each cover assembly is associated with at least one gas handle 10. The first cover assembly 18 comprises a cover 32 that at least partially covers the handle 10. In some embodiments the cover 32 covers almost the entire handle 10. The cover 32 is able to be moved between different positions, namely between a covered position or uncovered position. In the uncovered position, the handle 10 may be more easily removed from the terminal 2. In FIG. 2, the cover 32 is shown in a covered position. The cover 32 may be made of any material. Non-limiting examples of materials include rigid and flexible materials, opaque and transparent materials, and variations thereof.

A sensor or a switch 28 is located near or on the cover 32 to detect the different positions of the cover 32. Alternatively, the sensor or switch 28 may be located near the handle 10 to detect the position of the handle 10. For example, the handle 10 may be in an unused position and resting on the support 12, or the handle 10 may be in a used position and removed from the support 12. It can be appreciated that many gas pump terminals 2 have sensors or switches already built into the terminal 2 for detecting whether or not the handle 10 is resting in the unused position. The signals from such built-in sensors may be incorporated into the sanitizing system for gas pump handles 10. The sensor or switch 28 may be a pressure sensor, a mechanical switch sensor, an infrared sensor, a magnetic field sensor, a light beam sensor, etc. It can be appreciated that any sensor device that can detect different positions of the cover 32, or the removal or presence of the handle 10 in the gas terminal 2, or both, is applicable to the principles described herein.

Located on the cover 32 is at least one spray nozzle or fogger 30 that dispenses sanitizer onto the handle 10. The spray nozzle or fogger 30 may be located on the inside of the cover 32 and so that the direction of the spray or fog is oriented towards the handle 10. In the embodiment shown, there are two spray nozzles or foggers 30 located on the cover 32.

Continuing with FIG. 2, the second handle cover assembly 16 also comprises a cover 20, a sensor or switch 26 and at least one spray nozzle or fogger 22. These components operate in a similar manner to those described with respect to the first handle cover assembly 18. It can be readily understood that for each gas handle 10, a handle cover assembly may be adapted to at least partially cover the handle 10. Therefore, if there are four gas handles 10, for example, there may be four handle cover assemblies.

The spray nozzles or foggers 30 on the first handle cover assembly 18 are in fluidic communication with a first pump 38. In particular, hosing or piping 34, shown in dotted lines, fluidly connects the pump 38 with each of the one or more spray nozzles or foggers 30. The hosing or piping 34 may be flexible to accommodate for movement of the cover 32 between different positions. Similarly, a second pump 40 is fluidly connected to one or more spray nozzles or foggers 22 on the second handle cover assembly 16 through hosing or piping 24. It can be readily understood that each handle cover assembly may be in fluidic communication with a pump.

Both the first and second pumps 38, 40 are also fluidly connected to a reservoir 44 which contains the sanitizer fluid. The hosing or piping between the reservoir 44 and the pumps 38,40 are shown in dotted lines. The reservoir 44 may be any vessel or tank suitable for storing sanitizer fluid. A controller 36 communicates with the pumps 38, 40 in order to control the flow of sanitizer dispensed through the nozzles or foggers 22, 30. The sensors or switches 26, 28 are also in communication with the controller 36.

In the embodiment shown in FIG. 2, the pumps 38, 40 are electrically powered and controlled. Similarly, the controller 36 may be an electrical device or computing device that exchanges data signals with the pumps 38, 40 in order to control the pumps. The sensors or switches 26, 28 also exchange data signals with the controller 36 in order to provide the controller 36 with information about the different positions of a certain cover 20, 32 or the positions of a certain handle 10. The controller 36 may also receive data signals from the user interface 5 on the terminal 2, wherein the data signal from the user interface 5 relate to, for example, whether a user has selected a certain type of gas or paid for the gas.

The settings or parameters that determine the behaviour of the controller 36 may reside directly within the controller 36, or may reside within a memory device 37 which is in data communication with the controller 36. It can be appreciated that the exchange of data between the controller 36, pumps 38, 40, sensors or switches 26, 28, and the memory 37 may take place over wireless mediums (e.g. Bluetooth™, infrared, radio) or wired mediums (e.g. electrical wires), or both. A power supply 42 supplies electrical power to the pumps 38, 40 and the controller 36. The controller 36, pumps 38, 40, memory 37, reservoir 44 and power supply 42 may located either within the terminal 2 or external to the terminal 2. Alternatively, certain of these components may located external to the terminal 2, while other may be located within the terminal 2.

In another embodiment, not shown here, there may be a single pump that is in communication with each of the handle cover assemblies. The single pump would be able to pump and divert sanitizer fluid to different handle cover assemblies, for example, one at a time. The controller 36 would determine which of the handle cover assemblies should the single pump divert sanitizer fluid towards. Such a pump would have valves for diverting to different nozzles or sprayers. It can be appreciated that various configurations of pumps and reservoirs for dispensing fluid are applicable to the principles described herein.

The sanitizer fluid may be stored in outdoor conditions and have low freezing temperatures, so that it will remain as a fluid (e.g. a liquid) even in very cold temperatures. The sanitizer fluid may also be fast drying so that a user's hands do not become wet when touching a recently sanitized handle 10. A non-limiting example of a sanitizer that could be used in the described system is Alocsan™ surface sanitizer. It can be appreciated that any sanitizer suitable for sanitizing handles is applicable to the principles described herein.

Figure 3:
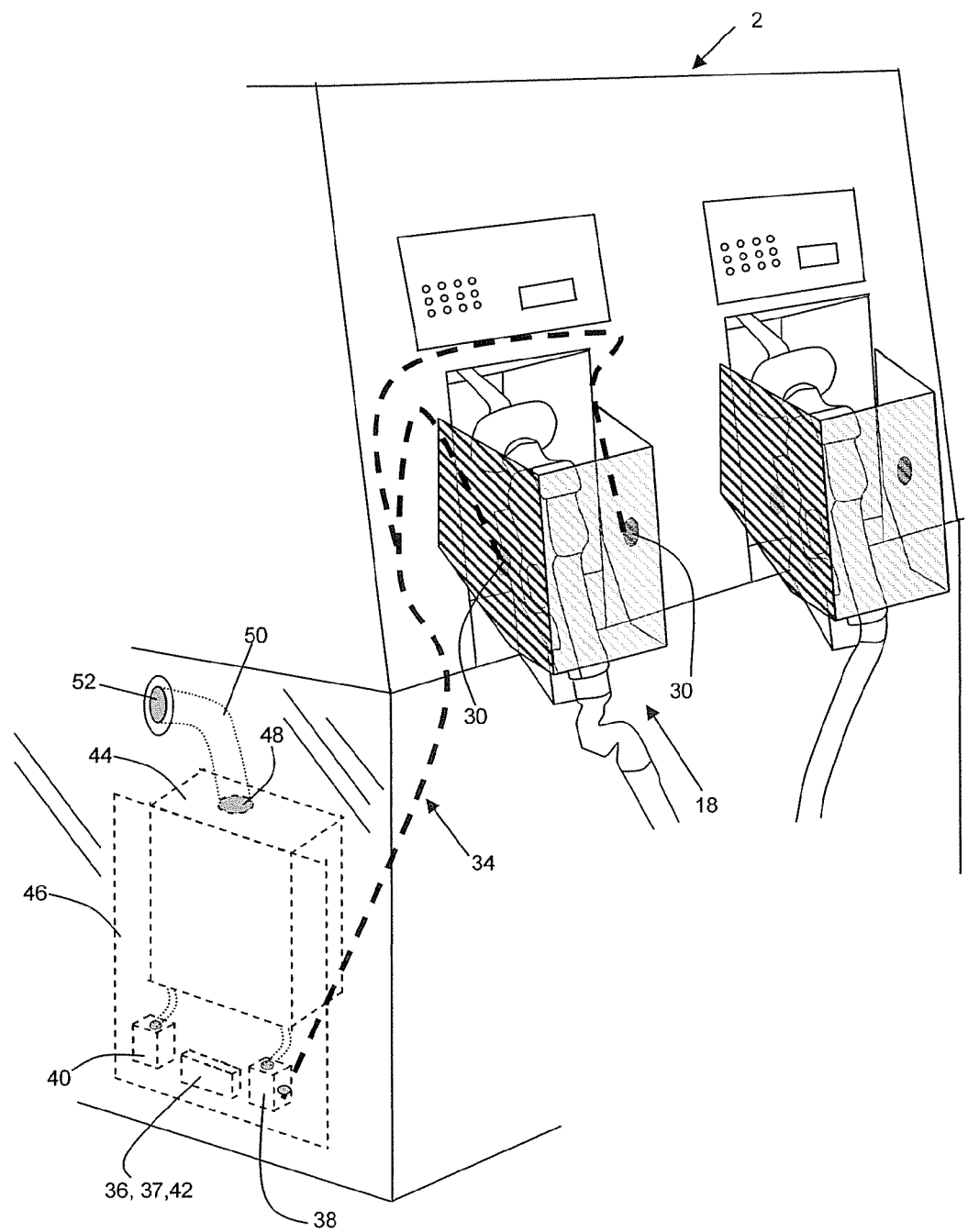
FIG. 3 is a schematic diagram of another embodiment of a system for sanitizing one or more gas pump handles.

Turning to FIG. 3, another embodiment of a sanitizing system for gas handles is provided, showing the relative positioning of the components. A mounting plate 46 is located on an inside wall of the terminal 2. Attached to the mounting plate 46 is the reservoir 44, pumps 40, 38, the controller 36, memory 37 and power supply 42. The mounting plate 46 allows for the components of the sanitizing system to be more easily installed into a gas pump terminal 2. When the reservoir 44 is located within the internal space of the terminal 2, a hose or pipe 50 connects an opening 48 at the reservoir 44 with a refill opening 52 at outer wall of the terminal 2. Thus, when sanitizer fluid is passed through the refill opening 52 of the terminal 2, the sanitizer fluid flows through the hose or pipe 50, and then through the opening 48 in the reservoir, thereby filling the reservoir 44. Such a configuration allows the components of the sanitizing system to be protected by the structure of the gas terminal 2, while allowing for the convenient refilling of the reservoir 44.

It can be appreciated that many of the components, such as for example, the cover 32, nozzle or foggers 30, the pump 38, the reservoir 44, the controller 36 and the sensor or switch 28, may be sold or packaged as a kit. The components may then be assembled and integrated into existing gas pump terminals 2. Thus, existing gas pump terminals 2 may be retrofitted or upgraded to include the features of the pump handle sanitizing system.

Alternatively, a gas pump terminal 2 may be built during the manufacturing stage to include the features of the pump handle sanitizing system.

Figure 4:
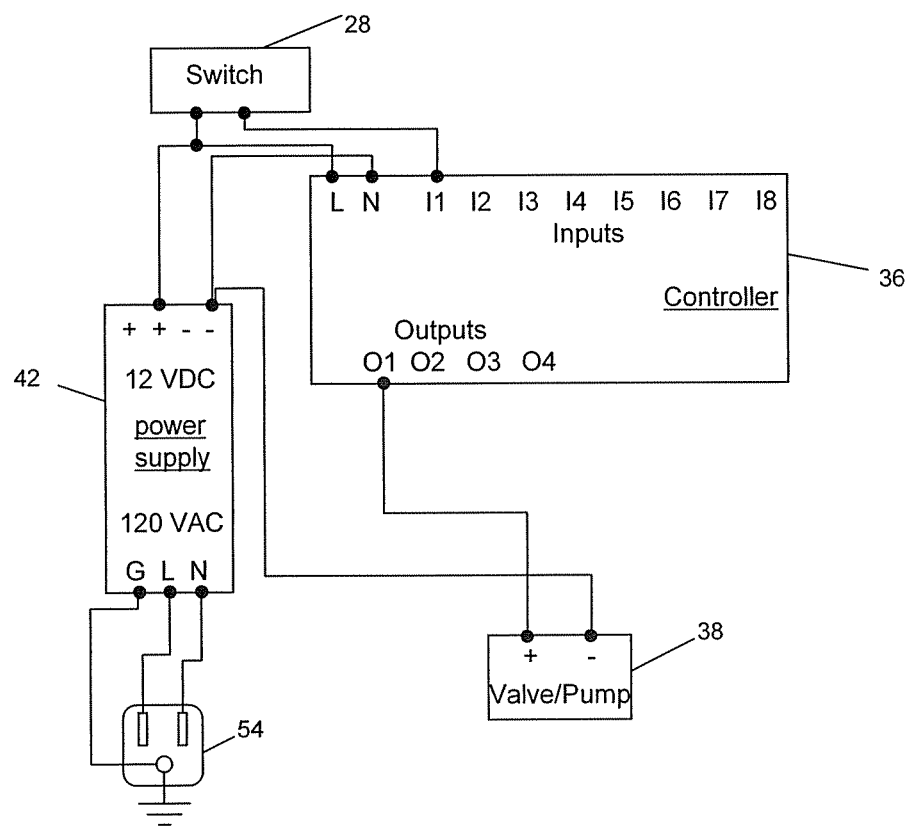
FIG. 4 is a schematic diagram of electrical components according to the embodiments of the system shown in any one of FIGS. 2 and 3.

Turning to FIG. 4, an embodiment of an electrical configuration for the sanitizing system is provided. The controller 36 has multiple inputs and outputs. The controller 36 may be selected to accommodate for the number of pumps and sensors or switches. In particular, the number of inputs on the controller 36 should accommodate the number of switches and the number of outputs should accommodate the number of pumps. In the embodiment shown in FIG. 4, a sensor or a switch 28 is electrically connected to an input of the controller 36. A pump 38, or a valve in the pump, is electrically connected to an output of the controller 36. The power supply 42 is electrically connected to the sensor or switch 28, the controller 36 and the pump 38. The power supply 42 may convert electrical power from a supply grid 54 (e.g. 120 VAC) to lower voltage energy (e.g. 12 VDC) suitable for the electrical components.

Continuing with FIG. 4, the switch 28, when closed, allows power to flow from the power supply 42, through the switch 28, to the input of the controller 36. The controller 36 will then receive a signal that the switch 28 is closed. Based upon such a signal, the controller 36 will decide whether or not, and when, the pump 38 is to be activated. When the controller 36 activates the pump 38, an electrical signal from the output of the controller 36 is sent to the pump 38.

In another embodiment, not shown here, existing controllers within the terminal 2 and existing sensors within the terminal 2 may be adapted to perform the function of the controller 36. In other words, an existing controller would be able to activate the pumps 38, 40, as well as receive signals from sensors.

It can be appreciated that other electrical configurations that connect a sensor or switch 28 to a controller 36, and connect a pump 38 to the controller 36 are applicable to principles described herein.

Figure 5:
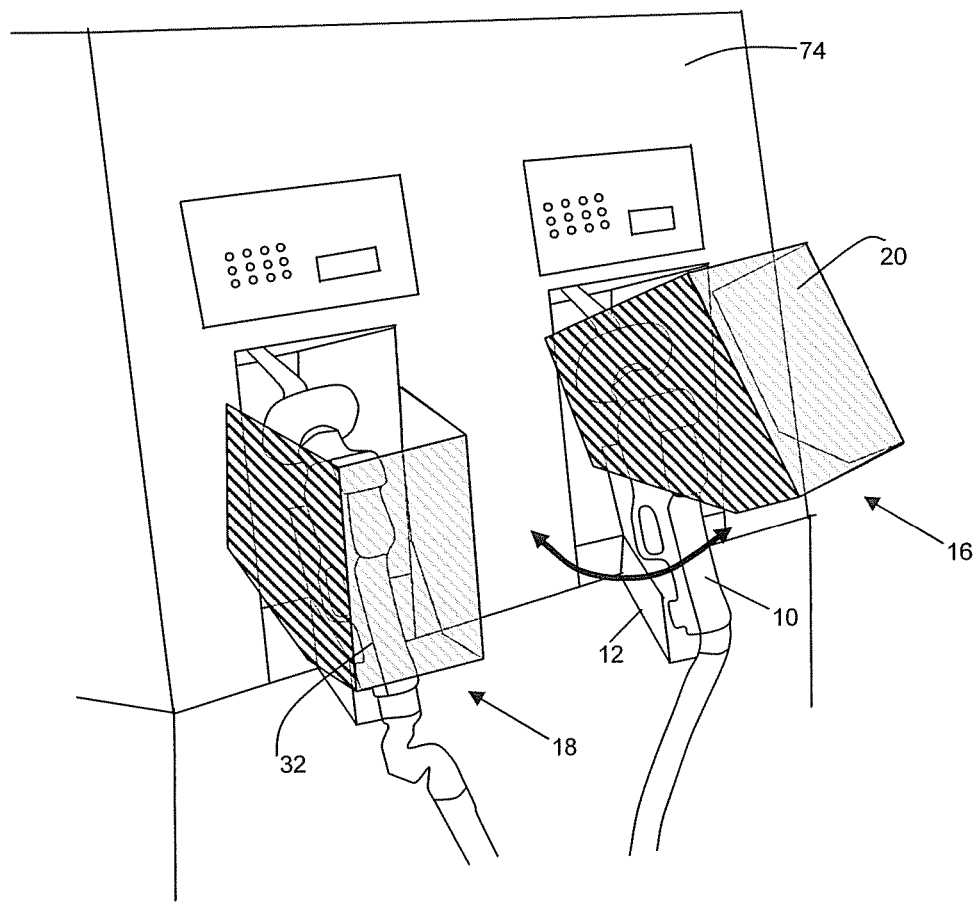
FIG. 5 is a schematic diagram of an embodiment of a system for sanitizing one or more gas pump handles with covers that are able to rotate between different positions.

FIGS. 5 to 9 show various other embodiments of the cover assembly and, in particular, a cover 32, 20. In FIG. 5, the first handle cover assembly 18 shows the cover 32 in a covered position, while the second handle cover assembly 16 shows the cover 20 in a different, i.e. uncovered position. In the covered position, the cover 32 partially encloses the handle 10 so that the spray nozzles or foggers 30 (not shown) are positioned to dispense sanitizer fluid at the handle 10. In the covered position, the cover 32 also acts as a wind barrier to reduce the effects of wind blowing away the sanitizer. The covered position also advantageously localizes or contains the spray area of the sanitizer. Thus, when a person stands next to the handle cover assembly 18, the chance that the person will be sprayed by sanitizer is reduced. In the embodiment shown in FIG. 5, the cover is able to rotate from a covered position to an uncovered position, as shown by the cover 20. It can be appreciated that a hinged mechanism connects the covers 32, 20 to the front face 74 of the terminal 2 in order to allow the covers 32, 20 to rotate between covered and uncovered positions. The cover 20 is shown rotating from a downwards to an upwards position. In the uncovered position, when the cover 20 is rotated upwards, the handle 10 is accessible and can be lifted off the support 12 for pumping gas.

Figure 6:
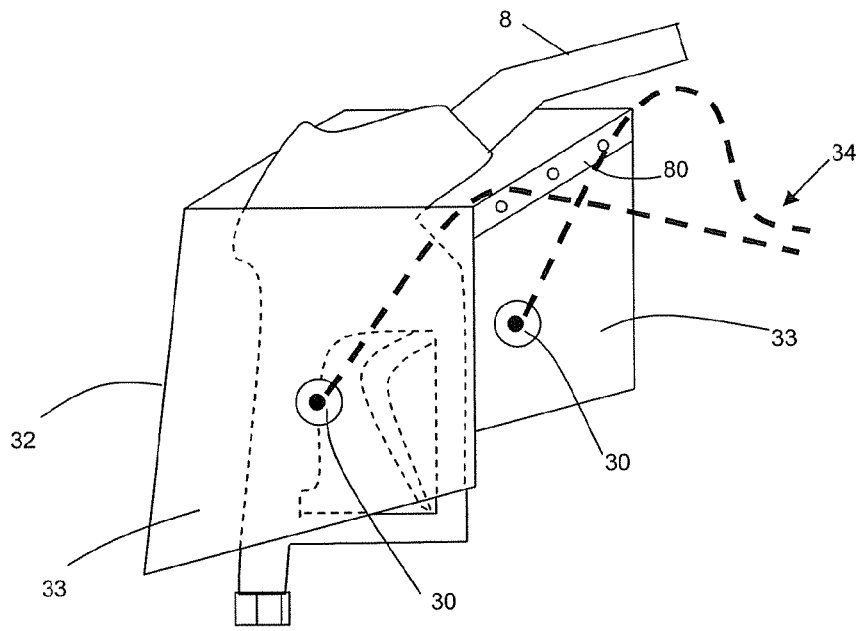
FIG. 6 is a schematic diagram of a gas pump handle and a cover in a covered position, shown in isolation.
Figure 7:
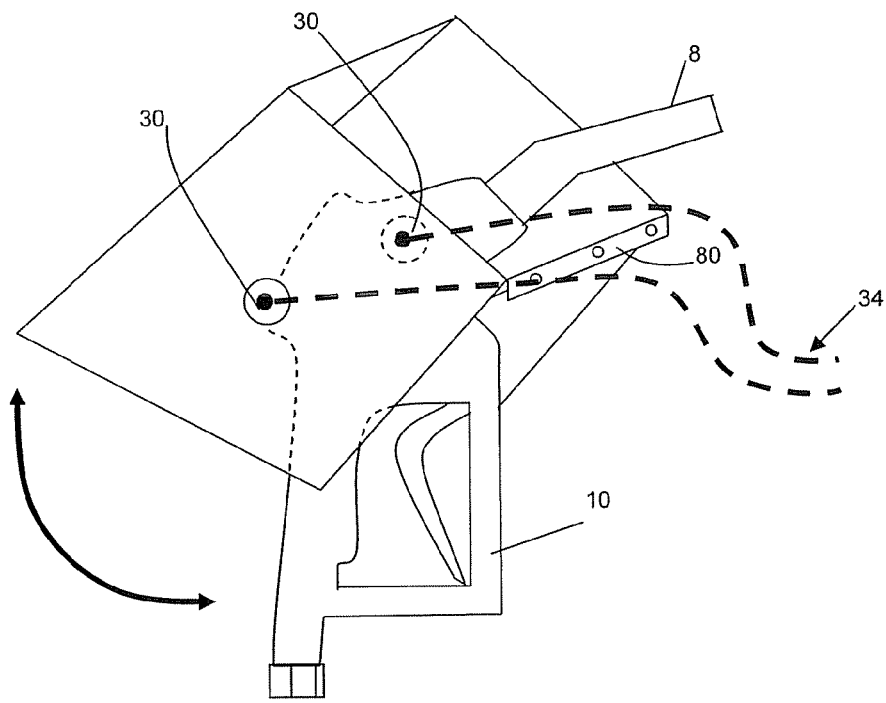
FIG. 7 is a schematic diagram of a gas pump handle and a cover shown in an uncovered position.

FIGS. 6 and 7 more clearly show the covered and uncovered positions of the cover 32, respectively. In FIG. 6, the cover 32 at least partially encloses the handle 10 and the spray nozzles or foggers 30 are positioned on the side panels 33 of the cover 32 so that the sanitizer fluid, when sprayed, is directed towards the handle 10. A hinge 80 is also shown spanning between two opposing corners of the cover 32. When the handle 10 is in the unused position at the terminal 2, the hinge 80 is located below the nozzle 8, so that the handle 10 and the nozzle 8 can be conveniently removed from the terminal 2 for pumping gas. It can also be seen that the hosing or piping 34 is configured to travel along the side panels 33 of the cover 32. The section of hosing or piping 34 located between the terminal 2 (not shown) and the cover 32 may be located near the hinge 80 so that the amount of "loose" or free-hanging piping or hosing is reduced, while allowing the cover 32 to rotate freely.

In FIG. 7, the cover 32 is shown in the uncovered position. The spray nozzles or foggers 30 are no longer directed towards the handle 10 when the cover 32 is in the uncovered position. It can be seen that a user may readily reach for the handle 10 and remove the handle 10 from the terminal 2 when the cover 32 is in the uncovered position.

Figure 8:
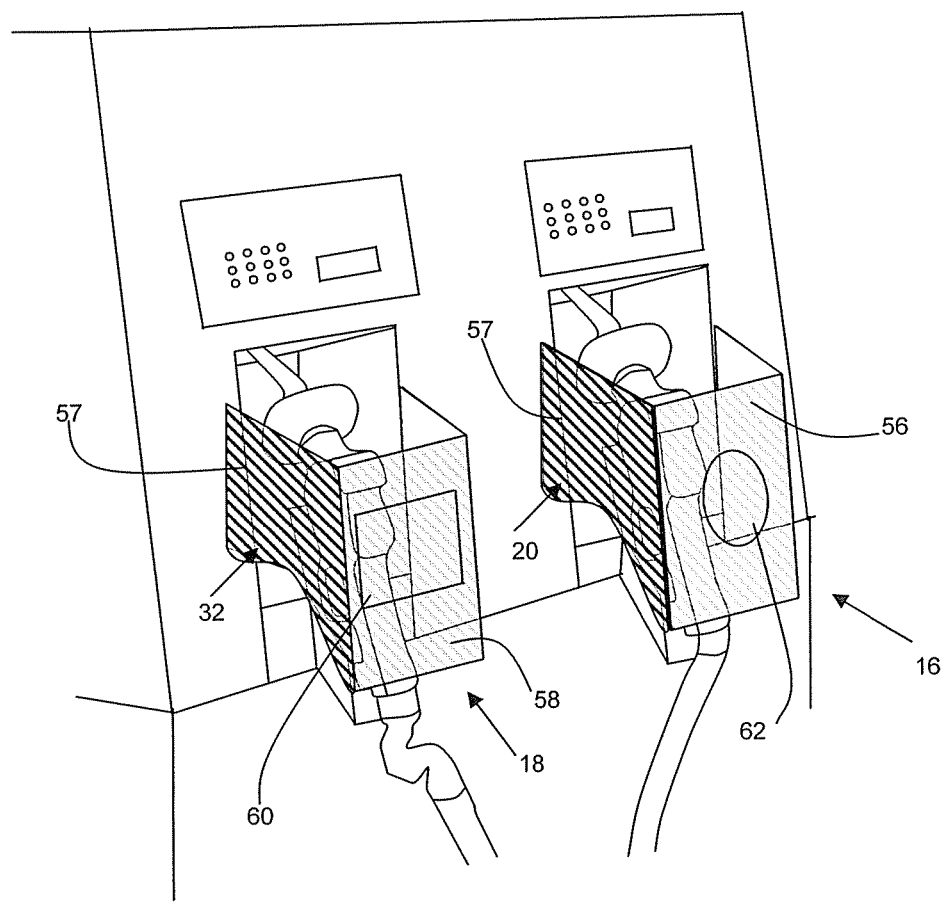
FIG. 8 is a perspective view of another embodiment of a system for sanitizing one or more gas pump handles.

FIG. 8 shows additional embodiments of the first and second handle cover assemblies 16, 18. Both assemblies 16, 18 have side panels 57 with a curved lower portion. The curved lower portion allows a user to more easily access and reach for the handle 10 when the cover 32, 20 is rotated upwards to an uncovered position. On the front face 58 of the cover 32, there is a display screen 60. The display screen 60 may be an LCD, an array of LEDs, or any other display device for showing various symbols and messages. It can be appreciated that the display screen 60 may be used to communicate information, such as the price of the gas, advertisements, temperature, the amount of sanitizer remaining in the reservoir 44, or combinations thereof. The display screen 60 may also be a touch screen for allowing the user to make certain selections, such as the type of gas to be purchased, the payment method, etc. Electrical wires would lead from the terminal 2 to the display screen 60, to provide both power and data. On the front face 56 of the other cover 20, there is advertisement space 62 for printed material (e.g. pamphlets, stickers, banners) to be placed. The advertisement space 62 may include a removable front plate so that different advertisements can be easily removed and replaced.

Figure 9:
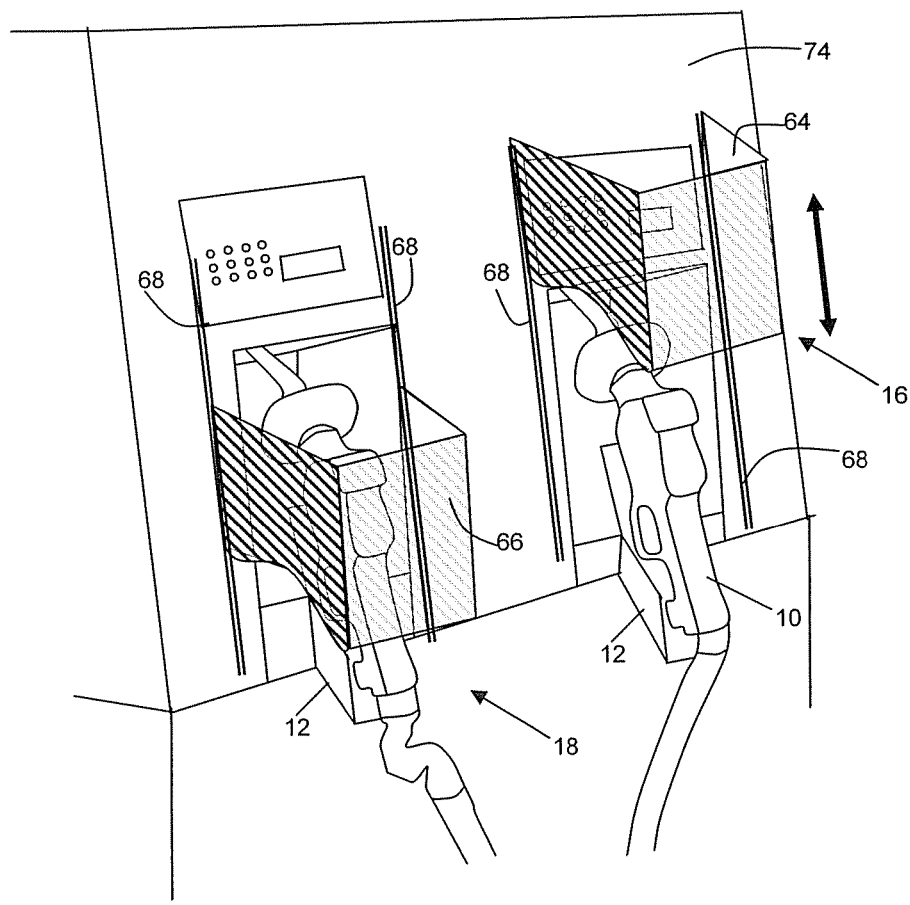
FIG. 9 is a perspective view of another embodiment of a system for sanitizing one or more gas pump handles with one or more covers that are able to slide between different positions.

FIG. 9 shows an alternate embodiment of the handle cover assemblies 16, 18. In the first handle cover assembly 18, a cover 66 is in a covered position, while in the second handle cover assembly 16, a cover 64 is in the uncovered position. A set of rails 68 are located on the front face 74 of the terminal 2. For each cover 64, 66, there are a pair of rails 68. The rails 68 are oriented in an upward and downwards fashion so that a cover 64, 66, that is slidably attached to the rails 68, is able to slidably move upwards and downwards between different positions. It can be appreciated that the edges of the cover 64, 66 that interface with the rails 68 may be equipped with rollers, guide hooks, or other sliding mechanisms to mechanically engage the rails 68. Any sliding mechanism that allows a cover 64, 66 to move between a covered position and an uncovered position is applicable to the principles described herein. The sliding mechanism would also allow for the spray nozzles or foggers (not shown in FIG. 9) to remain fluidly connected to the reservoir 44 when the cover 64, 66 is at least in the covered position.

It can be appreciated that the handle cover assemblies 16, 18 may be comprise any number of configurations for a cover that is able to move between a covered position and an uncovered position. Another example of such a configuration is a cover having swinging shutter doors or panels on the front face of cover, so that when the panels are opened, the handle 10 is uncovered and a user is provided access to the handle 10. The cover may also have various other geometries, such as curved or rounded shapes, triangular shapes, etc.

Figure 10:
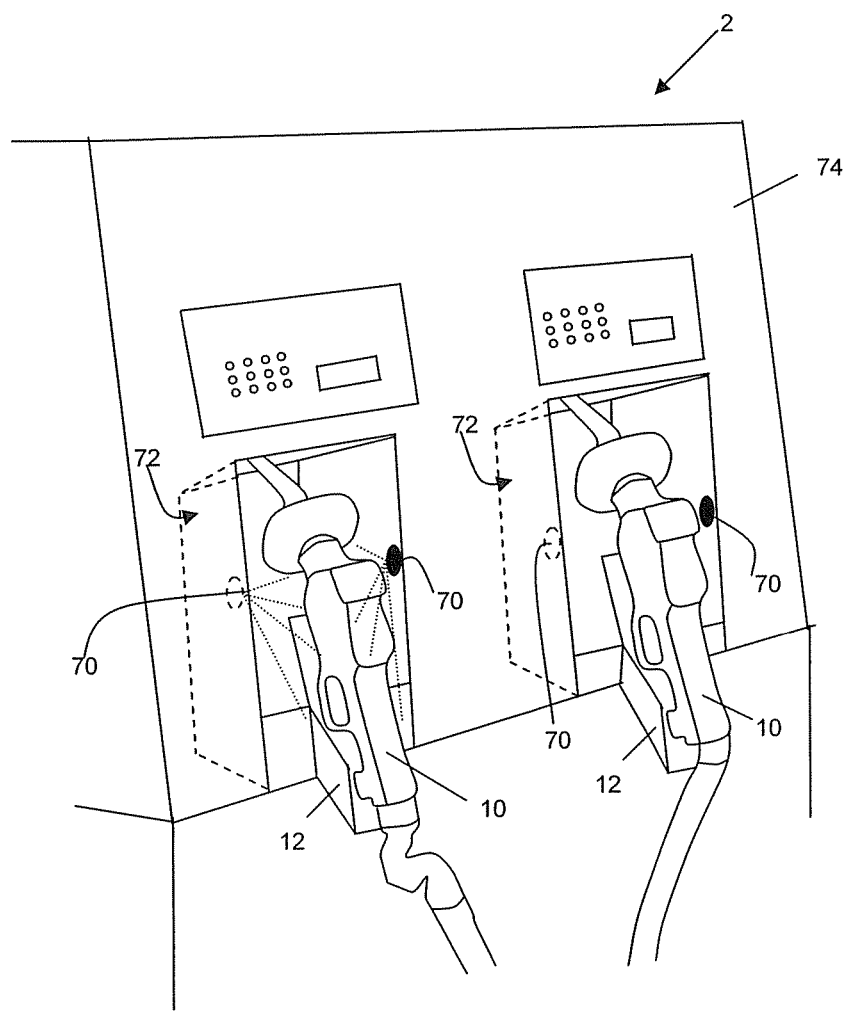
FIG. 10 is a perspective view of another embodiment of a system for sanitizing one or more gas pump handles without the use of a cover.

Turning to FIG. 10, an alternative embodiment is provided that does not require a cover. In the front face 74 of the terminal 2, there is a hollow 72 in which the pump handle 10 is positioned. One or more spray nozzles or foggers 70 are positioned within the hollow 72, so that they are oriented to dispense sanitizer fluid onto the handle 10. In one embodiment, the handle 10 may be positioned deep within the hollow 72. In another embodiment, the handle 10 may only be partially positioned within the hollow 72. In yet another embodiment, a cover (not shown) may enclose at least part of the handle 10 in combination with the hollow 72. The cover may or may not be equipped with spray nozzles or foggers. It is noted that if spray nozzles or foggers are mounted on the cover, then the handle 10 would be sprayed or coated with sanitizer fluid from both the spray nozzles or foggers 70 located within the hollow 72, as well as the nozzles or foggers located on the cover.

The operation of the spray nozzles or foggers are controlled by the various computer executable instructions or algorithms executed by the controller 36. It will be appreciated that any module or component exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the controller 36 or accessible or connectable thereto. Any application or module herein described may be implemented using computer readable/executable instructions that may be stored or otherwise held by such computer readable media.

Turning now to FIGS. 11 to 15, a number of flow diagrams for implementing computer executable instructions are provided.

Figure 11:
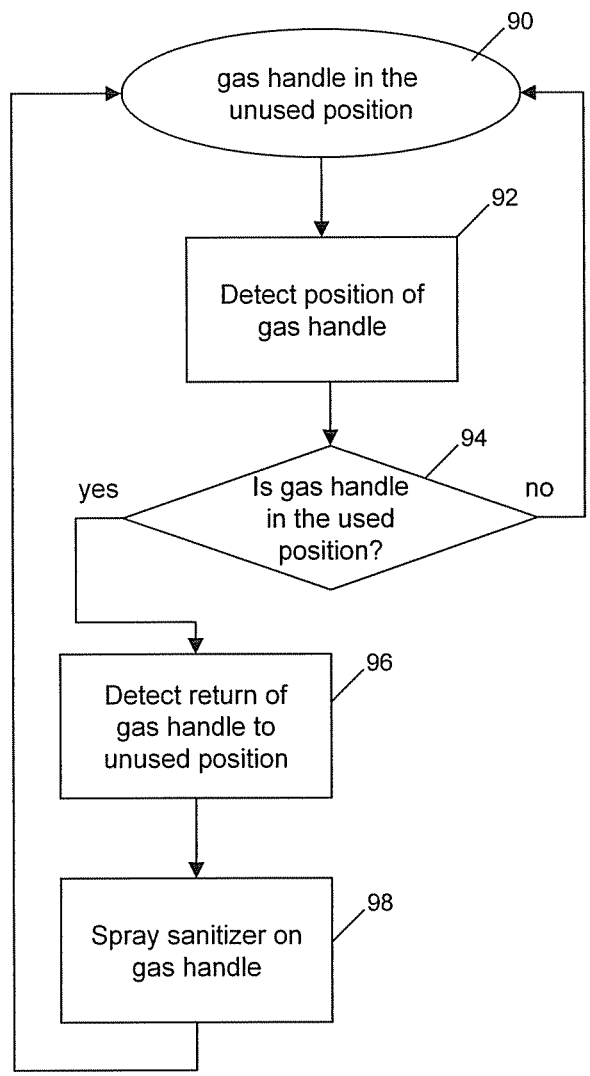
FIG. 11 is a flow diagram of a method for sanitizing a gas pump handle.

At FIG. 11, block 90 describes the state where the gas handle 10 is in the unused position. This position of the gas handle 10 is detected by a sensor or switch as described above. At block 92, the controller 36 detects, via the switch or sensor, the position of the gas handle 10. At block 94, if the gas handle 10 is in the used position, for example, no longer located at its resting position, then the controller 36 waits until it receives a signal from the sensor detecting the return of the handle 10 to the unused position (block 96). After it is detected that the handle 10 has been returned, then at block 98, the controller 98 sends a command to a pump to spray sanitizer on the handle 10. Block 98 exits to block 90, where the controller 36 detects the gas handle 10 in the unused position. If, at block 94, the handle 10 is detected to be in the unused position, then the controller 36 reverts back to the state provided at block 90.

It can be appreciated that after the sanitizer has been sprayed onto the handle 10, contaminants transferred on to the handle 10 will be killed or sanitized. Therefore, when another user touches the handle 10 next, the user will be touching a clean or sanitized handle.

Figure 12:
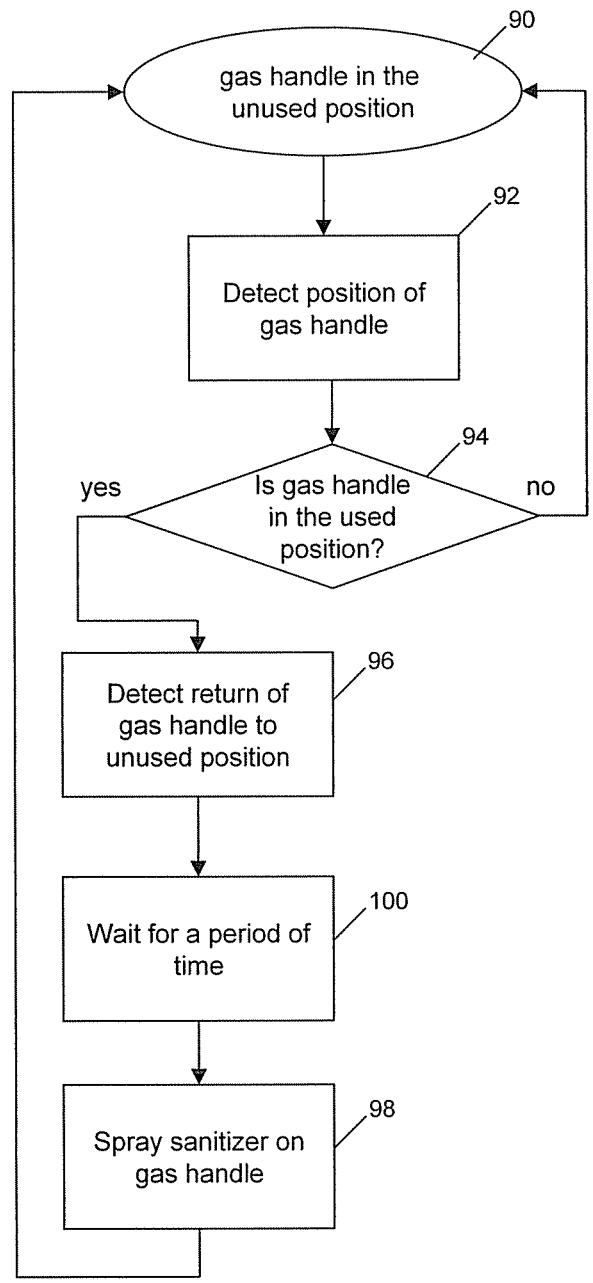
FIG. 12 is a flow diagram of another method for sanitizing a gas pump handle using a time delay.

FIG. 12 is very similar to FIG. 11. However, after detecting the handle 10 is in the used position (block 94) and upon detecting the return of the handle 10 to the unused position (block 96), the controller 36 waits for a period of time (block 100) before spraying the sanitizer (block 98). In one embodiment, the controller 36 waits for a period of time to allow the user to return the handle properly to the unused position and then remove their hand. In this way, the user's hand advantageously does not get sprayed by sanitizer while returning the handle 10 to its unused position. The time delay at block 100 may last roughly between two to four seconds.

Figure 13:
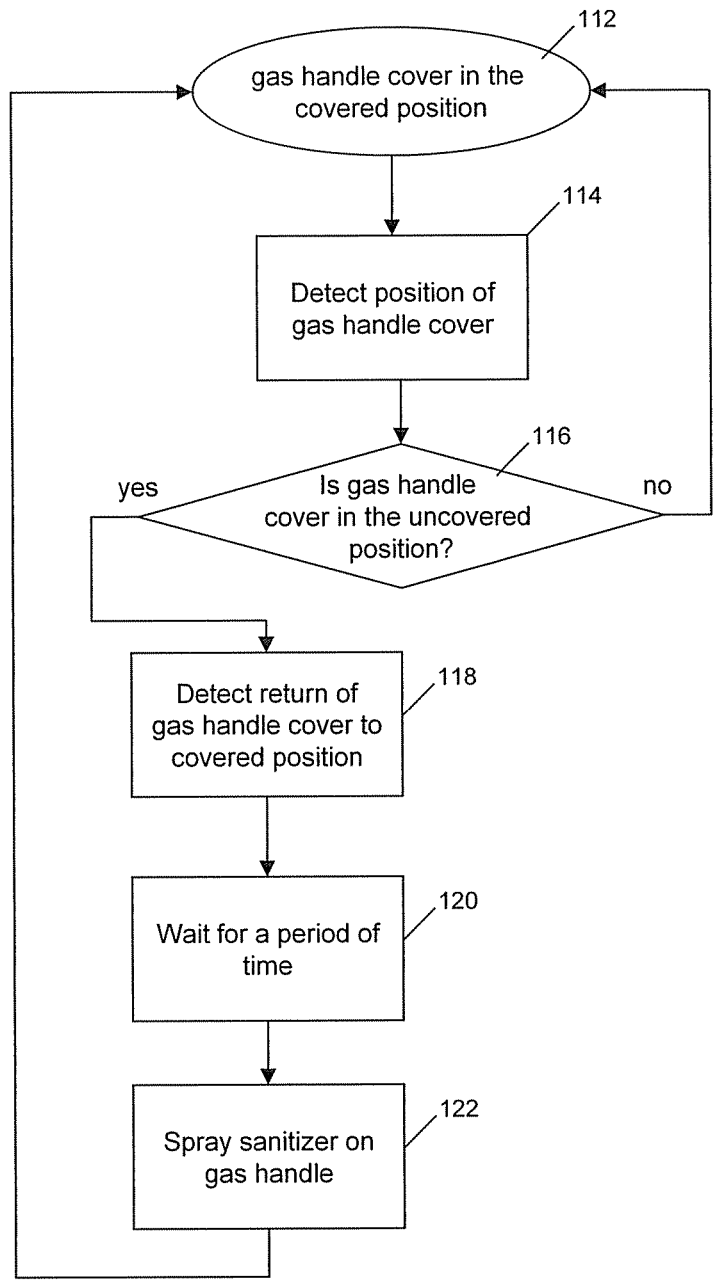
FIG. 13 is a flow diagram of a method for sanitizing a gas pump handle using the position of a cover.

FIG. 13 shows a series of instructions that are implemented for a sanitizing system having a cover 20 and a sensor or switch 26, 28 for detecting the position of the cover 20, 32. At block 112, controller 36 has determined that the state of a gas handle cover 20, 32 is in the covered position. The controller 36 detects, through a sensor or switch 26, 28, the present position of the cover 20, 32 (block 114). If the cover 20, 32 is in the uncovered position (block 116), then at block 118, the controller 36 waits for the return of the cover 20, 32 to the covered position. Once detecting the return of the cover 10 to the covered position (block 118), the controller 36 waits for a certain period of time (e.g. a time delay) (block 120) before sending a signal to the pump or pumps to spray the handle 10 (block 122). After the pumps are activated to spray an amount of sanitizer over a certain time, then the process loops again back to the state specified at block 112. At block 116, if the controller 36 has detected that the handle 10 is in the covered position, then the process is looped back to block 112.

Figure 14:
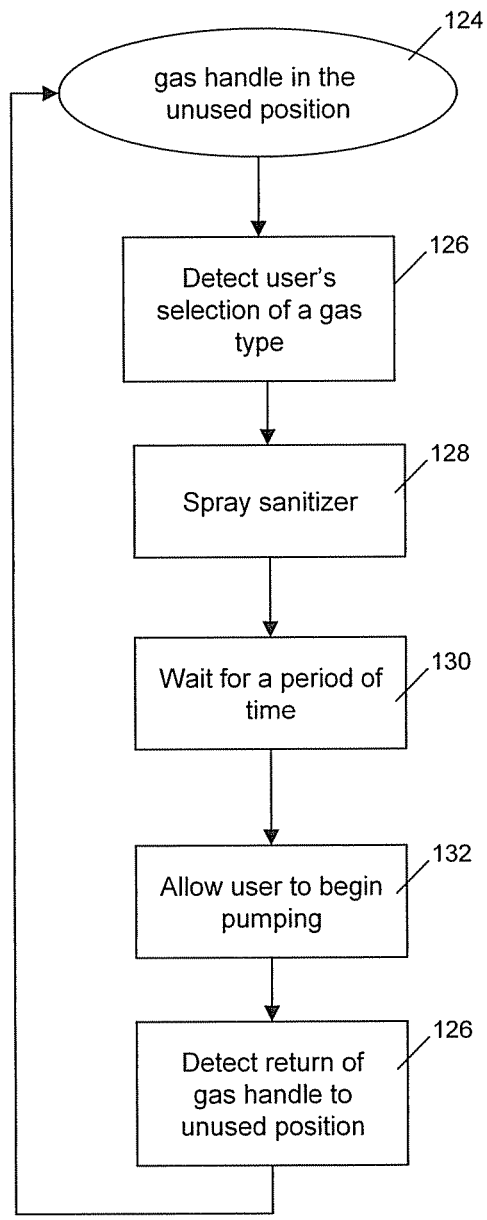
FIG. 14 is a flow diagram of a method for sanitizing a gas pump handle using a user's selection of a gas type.

FIG. 14 describes a process for spraying sanitizer based on detecting a user's selection of a gas type. At block 124, the controller 36 detects the current state of the handle 124 is in the unused position. At block 126, the controller 36 detects that the user has made a selection for a certain type of gas. The selection, for example can be made through the display screen 60 or through the user interface 5 located on the front face 74 of the terminal 2. The display screen 60 or the user interface 5 may have a computer (not shown) that detects the selection has been made, as currently used in the art. The computer would then send a signal to the controller 36 that a selection for gas has been made. Upon receiving the signal from the user interface 5 that a selection for gas has been made, the controller 36 activates or issues the command to the pump or pumps 38, 40 to spray the sanitizer onto the handle 10 (block 128). The controller 36 then waits for a period of time to allow the sanitizer to dry or evaporate (block 130) before allowing the user to begin pumping gas (block 132). At block 134, the controller 36 detects the return of the handle 10 to the unused position, for example, through a switch or sensor. The process loops back towards the state specified at block 124. This process may be applicable to sanitizing systems with covers, or without covers.

Figure 15:
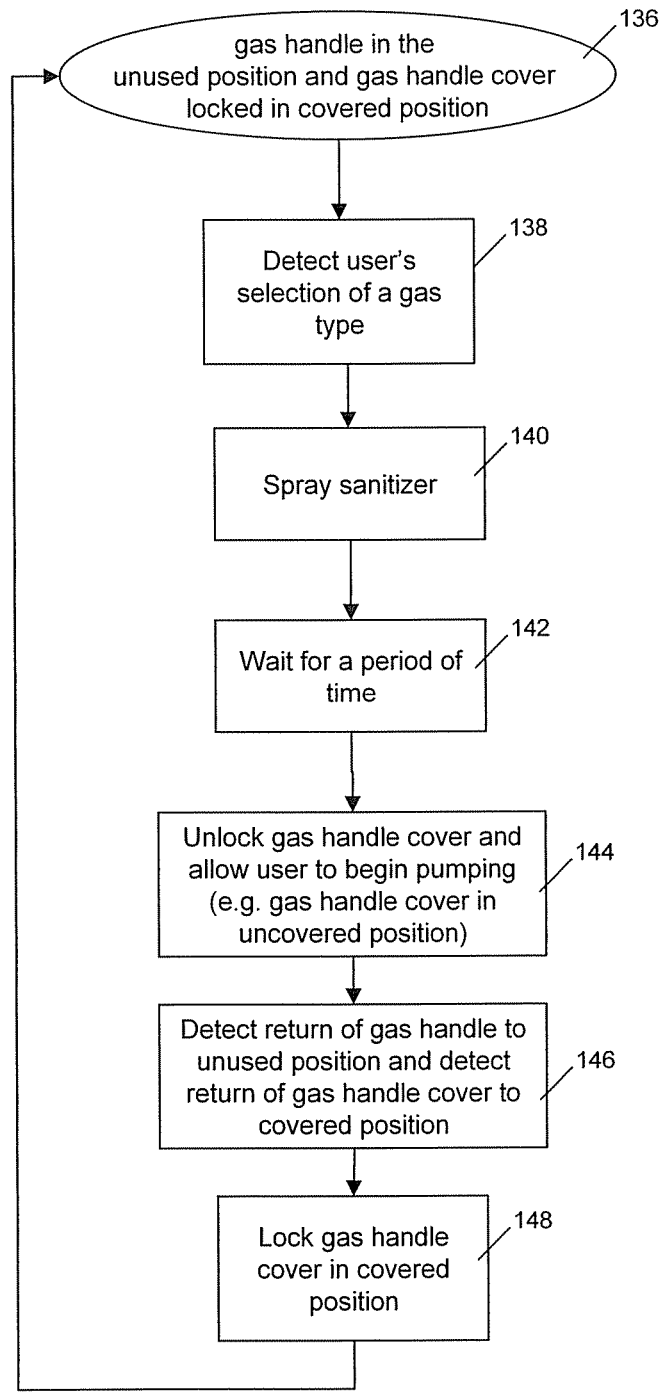
FIG. 15 is a flow diagram of another method for sanitizing a gas pump handle using a user's selection of a gas type.

FIG. 15 describes another process for sanitizing gas handles 10, requiring the use of a cover 20, 32. At block 136, the controller 36 detects the state of the handle 10 in an unused position and a cover 20, 32 locked into a covered position. Although not shown, it can be appreciated that various lock mechanisms (e.g. detents, latches, magnets, gears, etc.) can be used in combination with a cover 20, 32 to the lock the cover 20, 32 into a certain position. The lock mechanism should be electro-mechanical in nature such that the controller 36 can be in communication with and control the lock mechanism. At block 138, the controller 36 detects the user's selection of a type of gas through the user interface 5 or the display screen 60. At block 140, the controller 36 activates the pump or pumps to spray the sanitizer onto the handle 10. A period of time is passed (block 142) to allow for the sanitizer to at least partially dry. At block 144, the controller 36 unlocks the gas handle cover 20, 32 to allow the user access the handle 10. In other words, either automatically or manually, the cover 20, 32 is moved from a covered position to an uncovered position. The controller 36 then waits to detect the return of the handle 10 to the unused position and to detect the return of the cover 10 to the covered position (block 146). The controller 36 will either lock or detect the locking of the cover 20, 32 into the covered position, or both, as per block 148. The process then repeats, starting again with block 136. This process advantageously sanitizes the handle 10 before use. It also ensures that a user will not touch the handle 10 until the handle 10 is sanitized.

Although not shown, in another embodiment, ionization or electric discharge can be used to sanitize the gas pump handles 10. A device for generating electric current through handle 10 could be applied, while using a cover 32, 20 as well as a controller 36 for determining when the handle 10 should be sanitized.

It can thus be appreciated that there are a variety of methods for sanitizing a gas handle 10, either with or without a cover 20, 32. Certain of the above steps or instructions may be optional, and any such variations that ensure the handle 10 is sprayed with sanitizer are applicable to the principles described herein.

Figure 16:
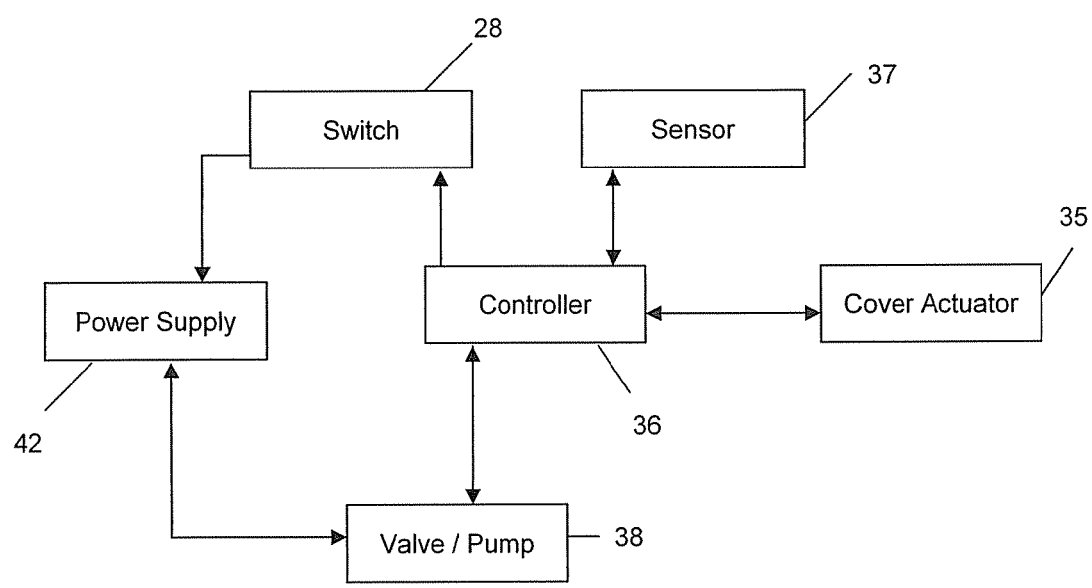
FIG. 16 is a block diagram of an embodiment of sanitizing system showing electrical and mechanical components, including an actuator for moving a cover of a gas pump handle.

FIG. 16 describes a sanitization system embodiment with a cover actuator 35. The cover actuator 35 may comprise one or more actuators. This is similar to the embodiment described in FIG. 4. However, in the embodiment in FIG. 16, an actuator 35 is able to automatically move the gas handle cover between a position covering the gas pump handle and a position uncovering the gas pump handle, or vice versa. This is triggered by a sensor 37 detecting the presence, proximity, or motion, or the like. In particular, at least one sensor 37 is connected to controller 36 and can detect a user's presence, motion, proximity, etc., for example using infrared sensors, light sensors, etc. It can be appreciated that sensors capable of detecting presence, motion, proximity, etc. can be used here. Upon detection, the sensor 37 relays a signal to controller 36. The controller 36 is then able to control the cover actuator 35 to move the cover between a covered position and an uncovered position, or vice versa. In other words, in general, the sensor 37 detects at least one of a user's presence, proximity and motion near the cover, and the actuator 35 is activated to move the cover depending on whether or not the sensor detects at least one of the user's presence, proximity and motion near the cover. It can be appreciated that various types of actuators may be used, including mechanical, electromechanical, pneumatic, and hydraulic type actuators, and combinations thereof.

Figure 17:
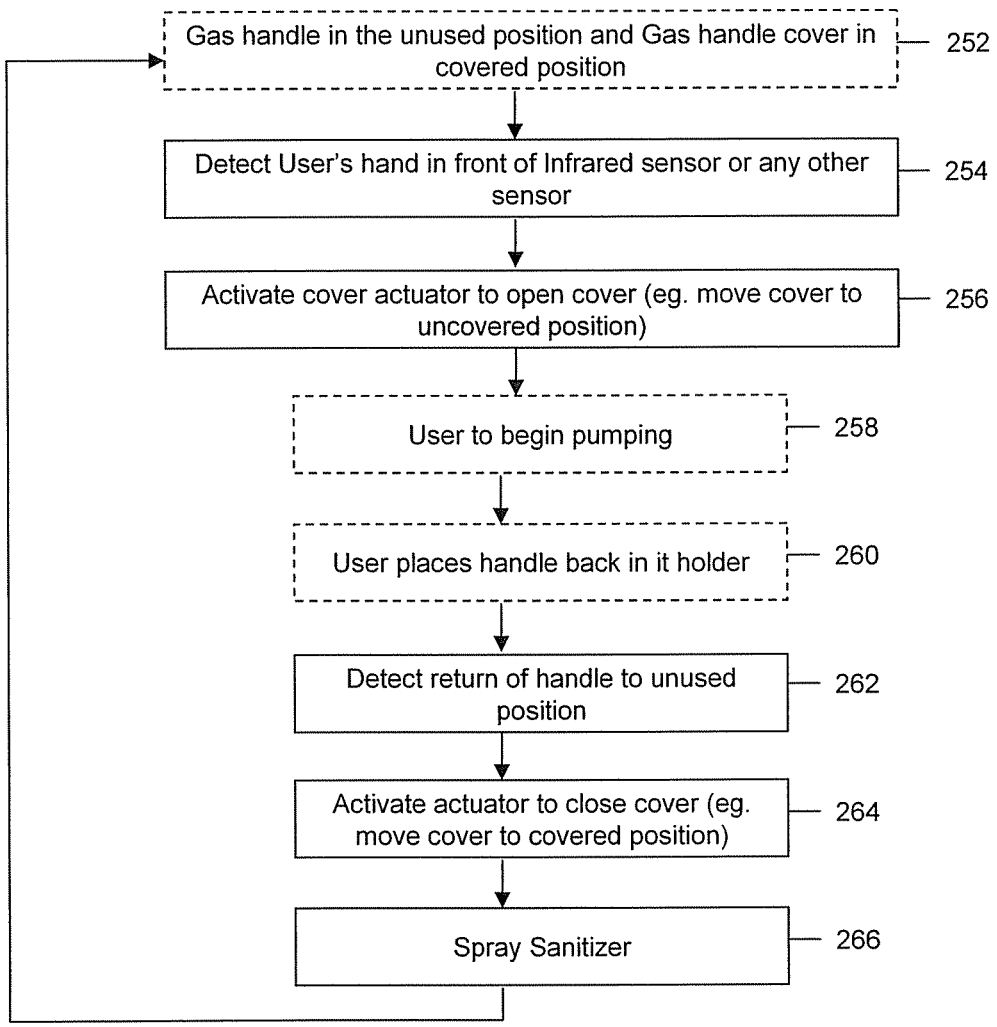
FIG. 17 is a flow diagram of a method for sanitizing a gas pump handle including activating a cover actuator to open or close the cover.

FIG. 17 describes a process for using the cover actuated sanitizing system. It can be appreciated that the controller 36 contains a computer readable medium for executing computer instructions, such as those described by way of example in FIG. 20. At block 252, the controller 36 detects a state whereby gas handle 10 and cover actuator 35 are in the unused position and the sensor 37 does not detect a user, such as a user's hand. At block 254, controller 36 receives a signal from sensor 37 that a user has been detected. At block 256, after receiving such signal, controller 36 activates cover actuator 35 to move the cover from a covered position to an uncovered position. When in the uncovered position, the user can access handle 10 and begin pumping fuel (block 258). After pumping is completed, the user returns handle 10 back onto support 12 (block 260). Upon return of gas handle 10, controller 36 detects via the switch or sensor that gas handle 10 is in unused position (block 262). Controller 36 then activates the cover actuator 35 to return cover from the uncovered position to the covered position (block 264). Controller 36 then issues a command to pump or pumps 38 to spray sanitizer through nozzles or foggers 30 (block 266). Block 266 then returns to block 252 where controller 36 detects gas handle 10 in the unused position. It can be appreciated that the blocks (e.g. blocks 252, 258, 260) shown in broken lines represent actions or states that are a result of a user's interaction.

Figure 18:
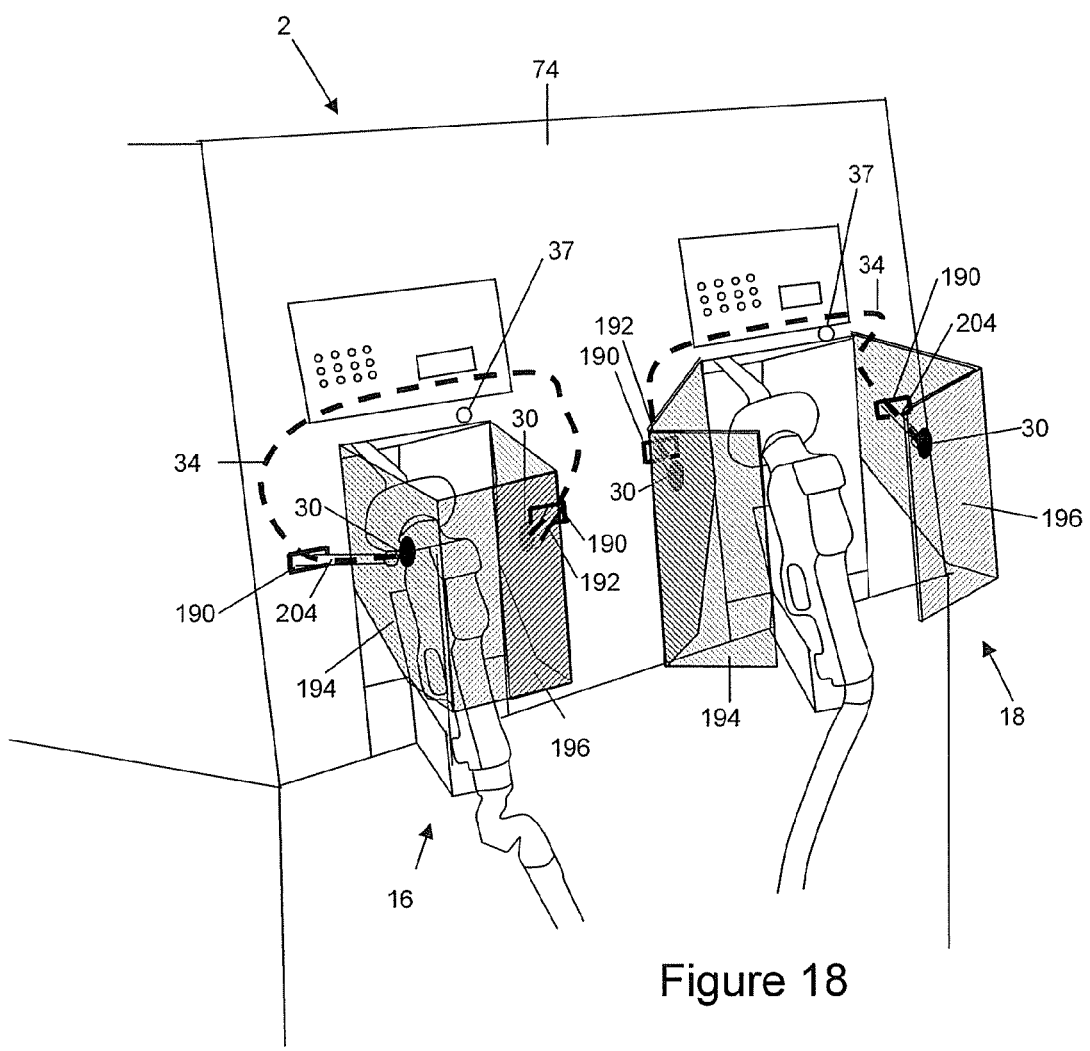
FIG. 18 is a perspective view of an embodiment of a system for sanitizing one or more gas pump handles with one or more covers using cover actuators.
Figure 19:
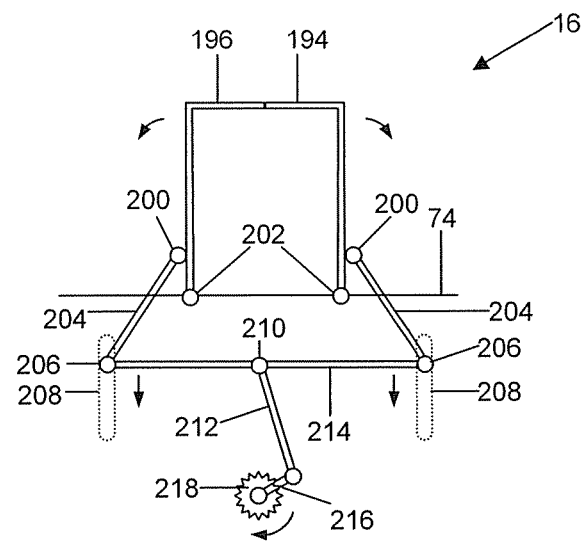
FIG. 19 is a plan view of the embodiment of the sanitization system shown in FIG. 18 in the covered position.
Figure 20:
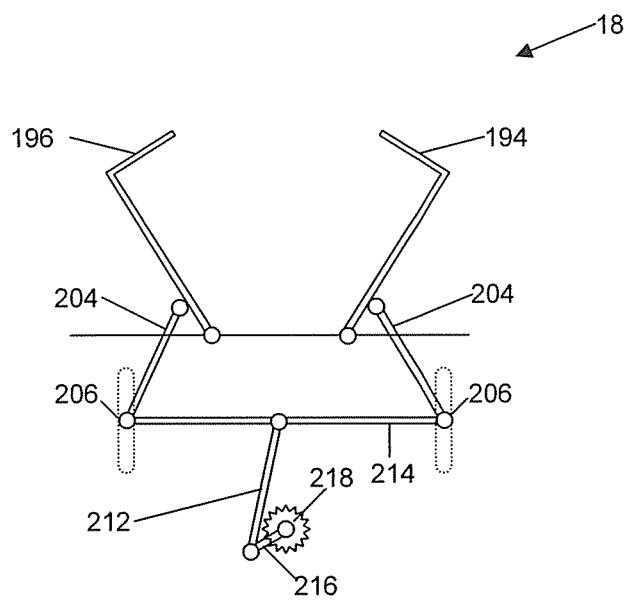
FIG. 20 is a plan view of the embodiment of the sanitization system using cover actuators shown in FIG. 18 in the uncovered position.

FIGS. 18, 19 and 20 show an alternate embodiment of the handle cover assemblies 16, 18 that are capable of automatically moving from a covered position to an uncovered position using, for example, one or more actuators 35 that are activated by sensor 37. In the first handle cover assembly 16, covers 194, 196 are closed together in a covered position, while in the second handle cover assembly 18, covers 194, 196 are apart in an uncovered position. Covers 194, 196 are rotatably attached to hinges 202, shown in FIGS. 19 and 20, located on the front face 74 of the terminal 2. The hinges 202 are oriented in an upward and downwards fashion so that covers 194, 196 are able to rotate towards each other and away from each other, for example, similar to swinging shutters. A linkage 204, also shown in FIGS. 19 and 20, is rotatably connected by hinge 200 to the outer side of each case 194, 196 facing away from the gas pump handle 10 of each cover assembly 16, 18. It can be appreciated that this connectivity may be located anywhere on the outer side of each case 194, 196. Linkage 204 passes through slotted opening 190 in the front face 74 to connect to the rest of the actuator system housed within. At least one spray nozzle 30 is attached to each case 194, 196 fluidly connected to hose 34 that runs from fluid reservoir 44. In one example embodiment, as best shown in FIG. 18, hose 34 is routed along linkage 204 to eliminate the need to create another slotted opening in front face 74. In another example embodiment, hose 34 is attached or flexibly connected to linkage 204 to eliminate possible clashing or rubbing with other components in use as well as eliminate need for a second slotted opening. This rotating mechanism would also allow for the spray nozzles 30 to remain at least fluidly connected to the reservoir 44 when covers 194, 196 are in the covered position.

FIG. 19 shows a top-down view of the embodiment shown in FIG. 18, whereby the cover is in a covered position. Cases 194, 196 are rotatably connected to hinges 202 fastened to the front face 74 of the gas pump. A linkage 204 is also rotatably attached to each case 194, 196 by hinge 200 on one end. Both linkages 204 are also rotatably connected to pull bar 214 by hinges 206. At least one hinge 206 is placed in guide 208 that restricts the movement of pull bar 206 to a linear fashion. It can be readily understood that guides 208 may consist of any mechanical means that restricts the motion of a pull bar 206 along a fixed path, and examples of such guides 208 include slotted grooves, guiding rails, systems of linkages or any combination thereof. Cam 212 is rotatably connected by hinge 210 to pull bar 214 on one end and rotatably connected to crank 216 on another. Crank 216 is also attached to motor 218. As motor 218 rotates crank 216, cam 212 also rotates forcing pull bar 214 to move either forwards or backwards depending on the position of the crank 216 and cam 212 at the time. As pull bar 214 moves backwards away from front face 74, linkages 204 pull cases 194, 196 apart at opposing angles thus moving towards the uncovered position, as shown in FIG. 20. As pull bar 214 moves towards the front face 74, linkages 204 push cases 194, 196 together towards the covered position as shown.

It can be readily understood that motor 218 may move in either a clockwise or counter clockwise fashion and is controlled by the controller 36. Motor 218 may also move in one direction to move from covered to uncovered position, and then reverse direction to back to covered position.

It can also be readily understood that motor 218 can be powered by electrical, hydraulic, pneumatic, or any other means that creates a circular rotational action.

FIG. 20 shows a top-down view of the cover actuator shown in FIG. 18 in the uncovered position. Cases 194, 196 are apart at similar but opposite angles relative to the front face 74 of the gas pump.

It can be readily understood that the angle of cases 194, 196 in the uncovered position can vary to include laying relatively flat along the front face 74 of the gas pump to any smaller angle that allows for the handle 10 to be removed from the handle assembly 18. The overall displacement of pull bar 214 between covered and uncovered position can also vary depending on the preferred angle of cases 194, 196 in the uncovered position or other design parameters.

It can be appreciated that the necessary angle of rotation required by crank 216 to move cases 194, 196 from covered to uncovered and again from uncovered to covered may vary and may not be equal, for example in a quick return embodiment.

Figure 21:
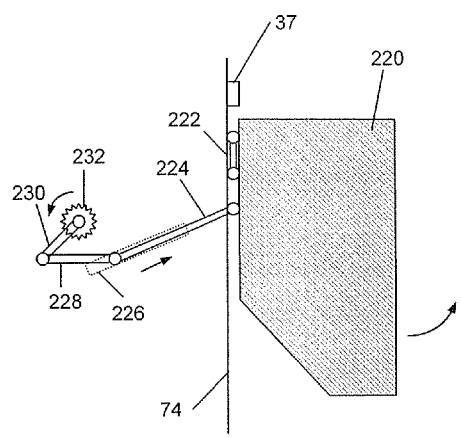
FIG. 21 is a side profile of another embodiment of a system for sanitizing one or more gas pump handles using cover actuators, with the cover in the covered position.
Figure 22:
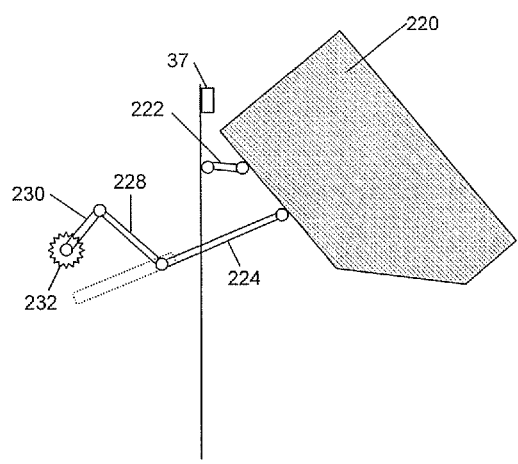
FIG. 22 is a side profile of the sanitization system shown in FIG. 21 with the cover in the uncovered position.

FIG. 21 shows a side profile of an alternate cover actuator embodiment with the cover in a covered position. Case 220 is rotatably attached to a pair of linkages 222 by hinges. Linkages 222 are also rotatably fastened to front face 74. Slider 224 is rotatably attached by hinge to case 220 and is constrained by guide 226. It can be readily understood that slider 224 may attach anywhere on case 220 including inner side facing gas pump handle 10 or outside. It can again be appreciated that guide 226 may consist of a slotted opening, rails, or any other mechanical means constraining the motion of slider 224 to a defined path. Rocker 228 is rotatably attached to slider 224 on one end and rotatably attached to crank 230 on the other. Crank 230 is attached to motor 232. As motor 232 turns cam 230, rocker 228 pushes slider 224 forcing case 220 to move forwards and rotate up, away from front face 74 towards the uncovered position as shown in FIG. 22. On the return, crank 230 pulls rocker 228 to pull on slider 224. Pulling slider 224 forces case 220 to move back towards the covered position as shown in FIG. 21.

It can again be readily understood that motor 232 may move in either a clockwise or counter clockwise fashion and is controlled by controller 36. Motor 232 may also move in one direction to move from covered to uncovered position, and then reverse direction to return back to covered position.

It can also be readily understood that motor 232 can be powered by electrical, hydraulic, pneumatic, or any other means that creates a circular rotational action.

FIG. 22 shows a side profile of the case actuator system shown in FIG. 21 in the uncovered position. Case 220 is pushed away from the front face 74 and rotated upwards to expose gas pump handle 10 (not shown).

It can be readily understood that the angle of rotation of case 220 may vary by design and may range from case 220 having its top side sitting relatively flush with front face 74 to any smaller angle with respect to front face 74 that allows for gas handle 10 to be removed from assembly 18.

It can again be appreciated that the necessary angle of rotation required by crank 230 to move case 220 from covered to uncovered and from uncovered to covered may vary and may not be equal.

Figure 23:
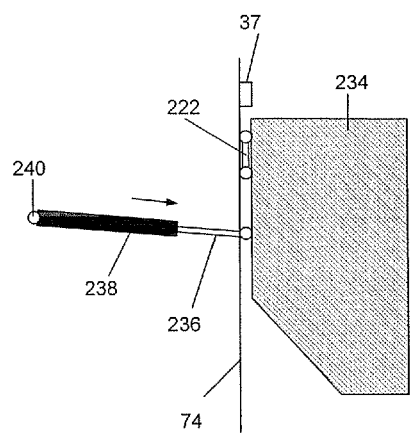
FIG. 23 is a side profile of another embodiment of a system for sanitizing one or more gas pump handles using cover actuators, with the cover in the covered position.

FIG. 23 shows a similar embodiment to FIG. 21 for handle cover assembly 16. Case 234 is similarly connected to linkage 222 as case 220. Case 234 is also rotatably connected to piston 236 which is connected to actuator 238. It can again be readily understood that piston 236 may be attached to case 220 anywhere including both inner side facing gas pump handle 10 and outside. Actuator 238 is rotationally pivoted by pivot 240. As actuator 238 pushes piston 238 out, piston 238 forces case 234 to rotate in a similar fashion case 220 described supra. This motion causes actuator 238 and piston 236 to rotate about pivot 240.

Figure 24:
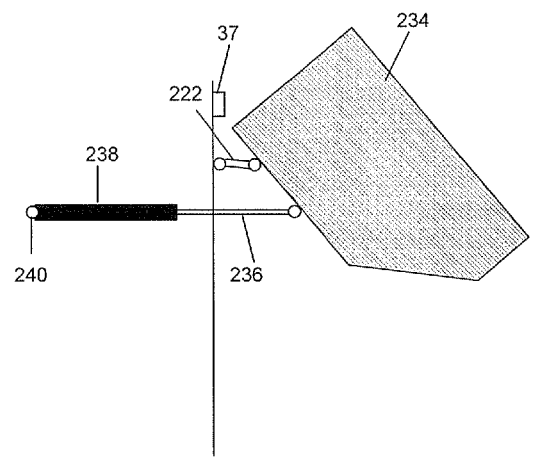
FIG. 24 is a side profile of the sanitization system shown in FIG. 23 with the cover in the uncovered position.

FIG. 24 shows a side profile of the automated positioning system shown in FIG. 23 in the uncovered position. Case 234 is pushed away from the front face 74 of the gas pump assembly 2 and rotated upwards to expose gas pump handle 10 (not shown).

It can be readily understood that to move piston 236 actuator 238 may be powered by hydraulics, pneumatics, etc.

Figure 25:
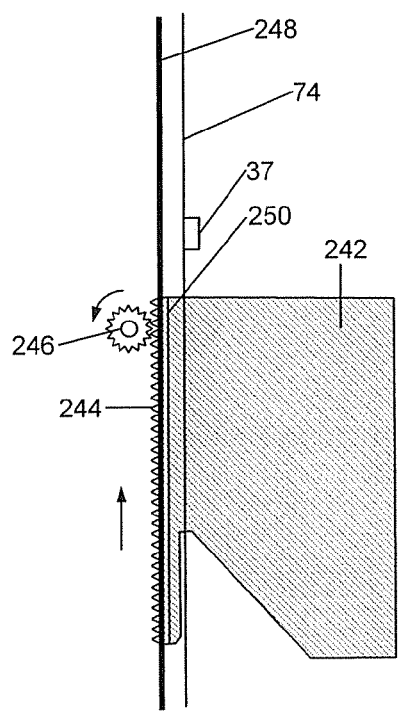
FIG. 25 is a side profile of another embodiment of a system for sanitizing one or more gas pump handles using cover actuators, with the cover in the covered position.

FIG. 25 shows a side profile of an alternate embodiment of the case actuator system, with the cover 242 in the covered position. Case 242 rests between at least one guide 250 mounted on front face 74. These guides may be composed of rails, slotted linkages, etc. Case 242 protrudes through at least one of the slotted grooves 248 in the front face 74. Several gear teeth 244 adorn one ridge of case 242 that mesh with rotary gear 246. As rotary gear 246 rotates case 242 is pushed upwards towards the uncovered position. Once case 242 is in the uncovered position, as shown in FIG. 26, rotary gear 246 must reverse direction to move case 246 back to covered position.

It can also be readily understood that rotary gear 246 can be powered by electrical, hydraulic, pneumatic, or any other means that creates a circular rotational action.

It can be readily understood that the motion of case 242 is not limited to a purely linear fashion. The teethed ridge of case 242 and guides 250 may be designed in an arched fashion that cause case 242 to move up and away from face 74 when moving towards the uncovered position.

Figure 26:
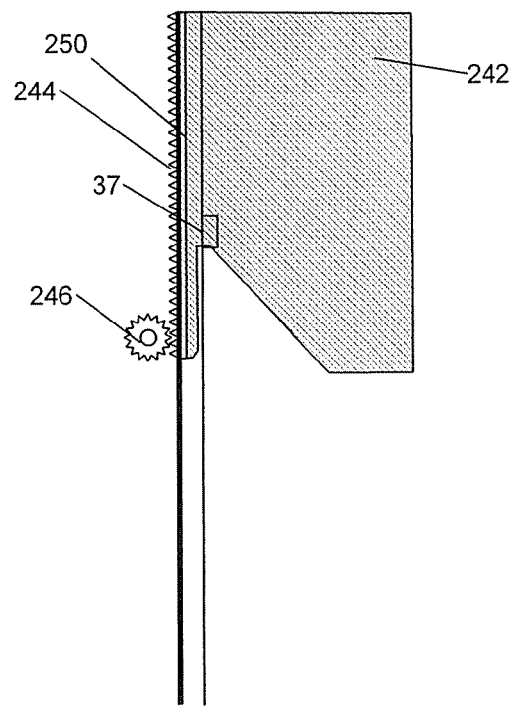
FIG. 26 is a sectional view the sanitization system shown in FIG. 25 with the cover in the uncovered position.

FIG. 26 shows a side profile of the embodiment shown in FIG. 25 in the uncovered position. Case 242 is pushed up along the front face 74 to expose gas pump handle 10 (not shown).

It can therefore be appreciated that various actuator configurations are used to move the cover between a covered position and an uncovered position. This advantageously allows the user to touch or handle a sanitized gas pump handle 10 without having to touch or handle an unsanitized cover. In other words, the number of surfaces the user needs to touch to pump gas is reduced, thereby decreasing the risk of coming in contact with germs.

Although the above has been described with reference to certain specific embodiments, various modifications thereof will be apparent to those skilled in the art without departing from the scope of the claims appended hereto.

The invention claimed is:

1. A system for sanitizing a pump handle comprising:
    a cover attachable to a pump terminal and configured to at least partially enclose said pump handle;
    a component of a sanitizing device positioned on said cover and oriented to sanitize said pump handle when said pump handle is resting at said pump terminal; and
    a controller for activating said sanitizing device.

2. The system in claim 1 wherein said sanitizing device comprises:
    one or more nozzles positioned and oriented to dispense sanitizer on said pump handle;
    at least one pump fluidly connected to said one or more nozzles to pump sanitizer from a reservoir to said one or more nozzles; and
    said controller is configured to activate said at least one pump.

3. The system in claim 2 wherein said controller activates said at least one pump upon receiving a signal from a sensor for detecting the presence of said pump handle at said pump terminal, or from a user interface of said pump terminal.

4. The system in claim 3 wherein upon said controller receiving said signal from said sensor detecting that said pump handle has been removed from said pump terminal and then returned, said controller activates said at least one pump to spray sanitizer said pump handle.

5. The system in claim 4 wherein said controller waits for a period of time after receiving said signal before activating said at least one pump.

6. The system in claim 3 wherein upon said controller receives said signal from said user interface detecting that a user has selected a gas type for pumping, said controller activates said at least one pump to spray sanitizer on said pump handle.

7. A system for sanitizing a pump handle comprising:
    a cover attachable to a pump terminal, said cover able to move between a covered position and an uncovered position when attached to said pump terminal, said covered position at least partially enclosing said pump handle and said uncovered position allowing said pump handle to be accessed;
    one or more nozzles positioned on said cover and oriented to dispense sanitizer on said pump handle when said pump handle is resting at said pump terminal;
    at least one pump fluidly connected to said one or more nozzles to pump sanitizer from a reservoir to said one or more nozzles; and
    a controller for activating said at least one pump.

8. The system in claim 7 wherein said controller activates said at least one pump upon receiving a signal from a sensor for detecting at least one of said cover's position and the presence of said pump handle at said pump terminal.

9. The system in claim 8 wherein upon said controller receives said signal from said sensor detecting that said pump handle has been removed from said pump terminal and then returned, said controller activates said at least one pump to spray sanitizer on said pump handle.

10. The system in claim 8 wherein upon said controller receives said signal from said sensor detecting that said cover has been moved to said uncovered position and then returned to said covered position, said controller activates said at least one pump to spray sanitizer on said pump handle.

11. The system in claim 8 wherein said controller waits for a period of time after receiving said signal before activating said at least one pump.

12. The system in claim 7 wherein said cover, when attached to said pump terminal, is able to slide upwards or downwards between said covered position and said uncovered position.

13. The system in claim 7 wherein said cover, when attached to said pump terminal, is able to rotate upwardly or downwardly between said covered position and said uncovered position.

14. The system in claim 7 wherein said cover includes a display screen.

15. The system in claim 7 wherein said controller activates said at least one pump upon receiving a signal from a user interface of said pump terminal.

16. The system in claim 15 wherein upon said controller receives said signal from said user interface detecting that a user has selected a gas type for pumping, said controller activates said at least one pump to spray sanitizer on said pump handle.

17. The system in claim 7 further comprising at least one actuator configured to move said cover between said covered position and said uncovered position.

18. The system in claim 17 further comprising a sensor for detecting at least one of a user's presence, proximity and motion near said cover, wherein said at least one actuator is activated to move said cover depending on whether or not said sensor detects at least one of said user's presence, proximity and motion near said cover.

19. The system of claim 8 further comprising at least one actuator configured to move said cover between said covered position and said uncovered position, wherein upon said controller receiving said signal from said sensor detecting that said pump handle has been removed from said pump terminal and then returned, said actuator is configured to move said cover from said uncovered position to said covered position.

* * * * *